United States Patent [19]

Schmitt-Willich et al.

[11] Patent Number: 6,039,931
[45] Date of Patent: Mar. 21, 2000

[54] DERIVATIZED DTPA COMPLEXES, PHARMACEUTICAL AGENTS CONTAINING THESE COMPOUNDS, THEIR USE, AND PROCESSES FOR THEIR PRODUCTION

[75] Inventors: Heribert Schmitt-Willich; Johannes Platzek; Heinz Gries; Gabrielle Schumann-Giampieri; Hanns-Joachim Weinmann; Hubert Vogler; Julius Deutsch; Juergen Conrad, all of Berlin, Germany

[73] Assignee: Schering Aktiengesellschaft, Berlin, Germany

[21] Appl. No.: 08/319,357

[22] Filed: Oct. 6, 1994

Related U.S. Application Data

[62] Division of application No. 07/909,379, Jul. 6, 1992, abandoned, which is a continuation of application No. 07/809,830, Dec. 20, 1991, abandoned, which is a continuation of application No. 07/780,840, Oct. 23, 1991, abandoned, which is a continuation-in-part of application No. 07/544,530, Jun. 28, 1990, abandoned.

[30] Foreign Application Priority Data

Jun. 30, 1989 [DE] Germany ............... 39 22 005

[51] Int. Cl.$^7$ .............. A61K 49/00; C07F 5/00
[52] U.S. Cl. .................. 424/9.364; 534/16
[58] Field of Search ............ 534/15, 16; 424/9, 424/9.364

[56] References Cited

U.S. PATENT DOCUMENTS

| | | | |
|---|---|---|---|
| 3,994,966 | 11/1976 | Sundberg et al. | 260/518 |
| 4,339,426 | 7/1982 | Meares et al. | 424/1 |
| 4,622,420 | 11/1986 | Meares et al. | 562/443 |
| 4,647,447 | 3/1987 | Gries et al. | 424/9 |
| 4,652,519 | 3/1987 | Warshawsky et al. | 435/7 |
| 4,672,028 | 6/1987 | Olson | 435/5 |
| 4,824,986 | 4/1989 | Gansow | 558/17 |
| 4,880,008 | 11/1989 | Lauffer | 128/654 |
| 4,899,755 | 2/1990 | Lauffer | 128/654 |
| 4,916,246 | 4/1990 | Felder | 556/1 |
| 5,057,302 | 10/1991 | Johnson et al. | 424/1.1 |
| 5,101,041 | 3/1992 | Troutner et al. | 548/518 |
| 5,137,711 | 8/1992 | Weber et al. | 424/9 |
| 5,198,208 | 3/1993 | Berg et al. | 424/1.1 |
| 5,399,340 | 3/1995 | Radüchel et al. | 424/9 |
| 5,419,894 | 5/1995 | Gries et al. | 424/1.65 |
| 5,482,700 | 1/1996 | Deutsch et al. | 424/9.364 |

FOREIGN PATENT DOCUMENTS

| | | |
|---|---|---|
| 0 165 716 | 12/1985 | European Pat. Off. . |
| 0 263 059 | 4/1988 | European Pat. Off. . |
| 263059 | 4/1988 | European Pat. Off. . |
| 0263059 | 6/1988 | European Pat. Off. ...... C07C 103/50 |
| 0 299 795 | 1/1989 | European Pat. Off. . |
| 299795 | 1/1989 | European Pat. Off. . |
| 0 305 320 | 3/1989 | European Pat. Off. . |
| 0 315 220 | 5/1989 | European Pat. Off. . |
| 37 10 730 | 10/1988 | Germany . |
| 1374979 | 11/1974 | United Kingdom . |
| 88/07521 | 6/1988 | WIPO . |
| 89/05802 | 6/1989 | WIPO . |

*Primary Examiner*—John Kight
*Assistant Examiner*—Lara C. Kelley
*Attorney, Agent, or Firm*—Millen, White, Zelano, & Branigan, P.C.

[57] ABSTRACT

Compounds of general Formula I

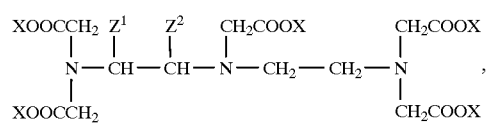

(I)

wherein
  $Z^1$ and $Z^2$ in each case independently mean the residue

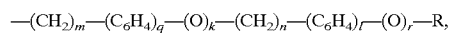

$$-(CH_2)_m-(C_6H_4)_q-(O)_k-(CH_2)_n-(C_6H_4)_r-(O)_r-R,$$

wherein
  m and n means the numbers 0–20,
  k, l, q and r means the numbers 0 and 1, and
  R means a hydrogen atom, an optionally $OR^1$-substituted $C_1$–$C_6$-alkyl residue, or a $CH_2COOR^1$ group with $R^1$ meaning it hydrogen atom, a $C_1$–$C_6$-alkyl residue, or a benzyl group,
X means a hydrogen atom and/or a metal ion equivalent of an element of atomic number 21–29, 42, 44 or 57–83,
with the provisos that at least two the substituents X stand for a metal ion equivalent; that one of the substituents $Z^1$ and $Z^2$ stands for a hydrogen and the other is not H; that—if n and l each mean the number 0—k and r do not simultaneously mean the number 1; that $-(O)_r-R$ is not $-OH$; and that $Z^1$ and $Z^2$ are not $-CH_2-C_6H_4-O-CH_2-COOCH_2C_6H_5$ or $-CH_2-C_6H_4-O-(CH_2)_5-COOCH_2C_6H_5$, as well as their salts with inorganic and/or organic bases, amino acids or amino acid amides, are valuable pharmaceutical agents, e.g., for NMR.

35 Claims, No Drawings

DERIVATIZED DTPA COMPLEXES, PHARMACEUTICAL AGENTS CONTAINING THESE COMPOUNDS, THEIR USE, AND PROCESSES FOR THEIR PRODUCTION

CROSS-REFERENCE TO RELATED APPLICATIONS

This application is a division of application Ser. No. 07/909,379, filed Jul. 6, 1992 (now abandoned), which is a continuation of Ser. No. 07/809,830, filed Dec. 20, 1991 (now abandoned), which is a continuation of Ser. No. 07/780,840, filed Oct. 23, 1991 (now abandoned), which is a continuation-in-part of Ser. No. 07/544,530, filed Jun. 28, 1990 (now abandoned).

BACKGROUND OF THE INVENTION

The invention relates to novel complexes and complex salts, agents containing these compounds, their use in diagnostics and therapy, as well as processes for preparing these compounds and agents.

Metallic complexes have been scrutinized as early as at the beginning of the fifties as contrast media for radiology. The compounds then employed were, however, of such toxicity that utilization on human patients could not be considered. It was, therefore, entirely surprising to find that certain complex salts exhibit adequate compatibility for considering routine administration to human patients for diagnostic purposes. The first representative of this class of compounds was the dimeglumine salt of Gd DTPA [gadolinium(III) complex of diethylenetriaminepentaacetic acid] described in the European Patent Application, Publication No. 71564, which proved itself very well in the form of a contrast medium for nuclear spin tomography. This compound has been registered, under the name of "Magnevist", worldwide as the first NMR diagnostic agent.

Contrast media exhibiting an at least partial extrarenal excretion would be desirable, in particular for patients with limited kidney function.

Consequently, there is a need for NMR contrast media exhibiting various pharmacokinetic behaviors.

SUMMARY OF THE INVENTION

The invention makes such compounds and media available, and also provides a process for their production.

The compounds according to this invention display renal elimination as well as excretion with feces.

Surprisingly, elimination via the gallbladder, however, is not the only extrarenal path of elimination: in NMR studies on rats, upon intravenous administration of the compounds of this invention, a contrast enhancement of the gastrointestinal tract has also been unexpectedly observed. The kidneys, as well as implanted tumors, are likewise visualized with improved contrast.

The elimination (secretion) by way of the stomach has the advantage that demarcation of abdominal structures (e.g., the pancreas) from the gastrointestinal tract is made possible, with a simultaneous contrast enhancement of pathological processes (tumors, inflammations). Imaging of the renal system, of the liver and gallbladder, and the bile ducts can moreover likewise be achieved. Besides the improved visualization of ulcers and stomach carcinomas, it is also possible to perform studies regarding gastric acid secretion with the aid of imaging procedures.

Accordingly, by making the compounds of this invention available, help can be extended to patients with renal insufficiency as well as patients suffering from gastrointestinal disorders (at least 10% of the population in the Western industrial countries). Most of these patients, as well as a large number of patients suspected of harboring such disease, must submit to diagnostic tests. At present, two methods suitable for this purpose are utilized above all: Endoscopy and X-ray diagnostics with the aid of barium contrast media.

These tests exhibit various drawbacks: they carry the risk of radiation stress, cause trauma, are connected with inconvenience, occasionally even with risk to the patient, and thus can evoke psychological stress. In most instances, these tests must be repeated; their performance is relatively complicated, require the patient's active cooperation (e.g., assumption of a specific bodily attitude) and frequently cannot be employed in case of frail and high-risk patients.

Provision of novel diagnostic methods for the identification and localization of gastrointestinal diseases, which methods do not exhibit these drawbacks, has thus likewise been attained by the complex compounds and agents according to this invention.

Their pharmacokinetics permits, even without specific measures, an improvement in the diagnosis of numerous diseases. The complexes for the most part are excreted again in unchanged form and rapidly so that, especially also in case of using relatively toxic metallic ions, no damaging effects are observed even at high dosage.

The practical use of the novel complexes is also facilitated by their favorable chemical stability.

The compounds of this invention are characterized by general Formula I

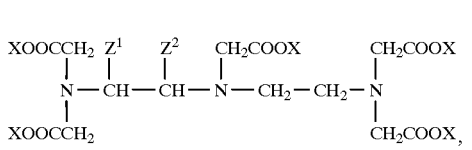

wherein $Z^1$ and $Z^2$ in each case independently mean the residue

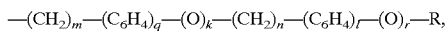

wherein m and n mean the numbers 0–20, k, l, q and r mean the numbers 0 and 1, and R means a hydrogen atom, an optionally $OR^1$-substituted $C_1$–$C_6$-alkyl residue, or a $CH_2$ $COOR^1$ group with $R^1$ meaning a hydrogen atom, a $C_1$–$C_6$-alkyl residue, or a benzyl group, X means a hydrogen atom and/or a metal on equivalent of an element of atomic numbers 21–29, 42, 44 or 57–83, with the proviso that at least two of the substituents X stand for a metal ion equivalent; that one of the substituents $Z^1$ and $Z^2$ stands for a hydrogen atom and the other is not H; that— if n and l each mean the number 0—k and r do not each simultaneously mean the nurber 1, that —$(O)_r$—R is not —OH; and that $Z^1$ and $Z^2$ are not —$CH_2$—$C_6H_4$—O—$CH_2$—$COOCH_2C_6H_5$ or —$CH_2$—$C_6H_4$—O—$(CH_2)_5$—$COOCH_2C_6H_5$, as well as their salts with inorganic and/or organic bases, amino acids or amino acid amides.

If the agent of this invention is intended for use in NMR diagnostics, then the central ion of the complex salt must be paramagnetic. These are, in particular, the divalent and trivalent ions of the elements of atomic numbers 21–29, 42, 44 and 58–70. Suitable ions are, for example, the chromium (III), manganese(II), iron(II), cobalt(II), nickel(II), copper (II), praseodymium(III), neodymium(III), samarium(III) and ytterbium(III) ions. On account of their very strong magnetic moment, the gadolinium(III), terbium(III), dysprosium (III), holmium(III), erbium(III) and iron(III)ions are especially preferred.

If the agent of this invention is meant for X-ray diagnostics, then the central ion must be derived from an element of a higher atomic number in order to obtain adequate absorption of the X-rays. It has been found that suitable diagnostic media for this purpose are those containing a physiologically compatible complex salt with central ions of elements of atomic numbers between 21–29, 42, 44, 57–83; these are, for example, the lanthanum(III) ion and the above-cited ions of the lanthanide series.

The numbers standing for m and n are preferably 0 to 5.

Suitable as the alkyl substituents R and $R^1$ are straight-chain or branched hydrocarbons of up to 6, preferably up to 4 carbon atoms which, in case of R, are optionally substituted by one or several, preferably 1–3, hydroxy or $C_1$–$C_6$-, preferably $C_1$–$C_4$-alkoxy groups.

Examples that can be cited for optionally substituted alkyl groups are the methyl, hydroxymethyl, ethyl, 2-hydroxyethyl, 2-hydroxy-1-(hydroxymethyl)ethyl, 1-(hydroxymethyl)ethyl, propyl, isopropyl, 2- and 3-hydroxypropyl, 2,3-dihydroxypropyl, n-, sec- and tert-butyl, 2-, 3- and 4-hydroxybutyl, 2- and 3-hydroxyisobutyl, pentyl, 2-, 3- and 4-hydroxy-2-methylbutyl, 2,3,4-trihydroxybutyl, 1,2,4-trihydroxybutyl, cyclopentyl, cyclohexyl, 2,3,4,5,6-pentahydroxyhexyl groups as well as—in case of the hydroxyalkyl groups—their $C_1$–$C_6$-, preferably $C_1$–$C_4$-alkyl derivatives, i.e., the corresponding $C_{1-6}$-alkoxy groups.

Preferred substituents $Z^1$ and $Z^2$ are the —$CH_2$—$C_6H_4$—$OCH_3$, —$CH_2$—$C_6H_5$, —$CH_2$—$C_6H_4$—O—$CH_2$—$C_6H_4$—$OCH_3$, —$CH_2$—O—$CH_2$—$C_6H_5$, —$CH_2$—$C_6H_4$—O—$CH_2$—COOH, —$CH_2$—$C_6H_4$—$OC_2H_5$, —$CH_2$—$C_6H_4$—$OC_4H_9$, —$CH_2$—$C_6H_4$—O—$CH_2$—$C_6H_5$ residues. Thus, m preferably is 1, and/or q preferably is 1, k and/or r preferably is 1, etc., and two phenyl rings are preferably separated by —O—$CH_2$. etc.

In case not all of the acidic hydrogen atoms are substituted by the central ion, it is possible to replace one, several, or all remaining hydrogen atom(s) by cations of inorganic and/or organic bases or amino acids.

Suitable inorganic cations are, for example, the lithium ion, the potassium ion, the calcium ion, the magnesium ion and, in particular, the sodium ion. Suitable cations of organic bases are, inter alia, those of primary, secondary or tertiary amines, such as, for example, ethanolamine, diethanolamine, morpholine, glucamine, N,N-dimethyglucamine and, in particular, N-methylglucamine. Suitable cations of amino acids are, for example, those of lysine, of arginine, and or ornithine. Suitable cations of amino acid amides are lysine methyl amide, glycine ethyl amide and serine methylamide.

The production of the complex compounds of this invention in accordance with general Formula I takes place by converting, in a manner known per se, compounds of general Formula II

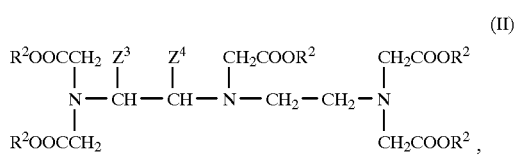

wherein
$R^2$ means an acid blocking group,
$Z^3$ and $Z^4$ each means a hydrogen atom or the residue —$(CH_2)_m$—$(C_6H_4)_q$—OH, with the proviso that one of the substituents $Z^3$ and $Z^4$ is a hydrogen atom and the other is the indicated residue, and m and q are as in Formula I
into a compound with the residue indicated for $Z^1$ and $Z^2$, splitting off the acid blocking groups $R^2$, reacting the thus-obtained complex-forming acids of general Formula I where X is a hydrogen atom (Formula I') with at least one metal oxide or metal salt of an element of atomic numbers 21—29, 42, 44 or 57—83, and subsequently—if desired—substituting any present acidic hydrogen atoms by cations of inorganic and/or organic bases, amino acids or amino acid amides.

Suitable acid blocking groups $R^2$ are lower alkyl, aryl and aralkyl groups, e.g. the methyl, ethyl, propyl, n-butyl, tert-butyl, phenyl, benzyl, diphenylmethyl, triphenylmethyl, bis (p-nitrophenyl)methyl groups, as well as trialkylsilyl groups.

Splitting off of the blocking groups $R^2$ takes place according to methods known to one skilled in the art [for example, E. Wünsch, "Methoden der Org. Chemie" [Methods of Organic Chemistry] (Houben-Weyl), vol. XV/1, 4th ed., 1974, pp 315 et seq.], for instance by hydrolysis, hydrogenolysis or alkaline saponification of the esters with an alkali in aqueous-alcoholic solution at temperatures of 0–50° C. Organic or inorganic acids are used for splitting off the tert-butyl esters which are especially advantageous for the present reactions: The ester compound dissolved in a suitable anhydrous organic solvent, but preferably the pulverized dry material, is combined either with a hydrogen halide solution in glacial acetic acid, with trifluoroacetic acid, or also with boron trifluoride diethyl etherate in glacial acetic acid and split off at temperatures of —10° C. to 60° C., preferably at room temperature.

The compounds of general Formula II, serving as educts for the production of the complex compounds of this invention, are known (DOS 3,710,730 and literature cited therein) or can be synthesized analogously to the preparation directions described therein. The entire disclosure of U.S. Ser. No. 07/430,442, now abandoned, (corresponding to the mentioned DOS), of Oct. 2, 1989, is hereby incorporated by reference herein.

A series of literature methods known to a person skilled in the art is available for reacting the known aliphatic or aromatic hydroxy compounds to the corresponding arylalkyl or dialkyl ethers (for example, J. March, Advanced Organic Chemistry, 3rd ed., 1985, pp 342 et seq.).

For this purpose, the compounds of Formula II wherein $R^2$ stands for an alkali-stable acid blocking group are dissolved in a polar aprotic solvent, such as, for example, tetrahydrofuran, dimethoxyethane or dimethyl sulfoxide, and combined with a base, such as, for example, sodium hydride, sodium hydroxide or alkali or alkaline earth carbonates, at temperatures of between –30° C. and the boiling point of the respective solvent, but preferably between 0° C. and 60° C.

A compound of general Formula III is added to this mixture

wherein Y means a nucleofugal entity, such as, for example, Cl, Br, I, $CH_3—C_6H_4SO_3$ or $CF_3SO_3$, and the remaining indices have the same meanings as in general Formula I.

The reaction periods are 30 minutes to 8 hours, depending on the steric hindrance of the residues participating in the reaction.

As an alternative to the aforedescribed reaction conditions, it is possible to produce arylalkyl as well as dialkyl ethers in a very advantageous way by phase transfer catalysis (Starks and Liotta, Phase Transfer Catalysis, Academic Press, N.Y. 1978, pp. 128—138).

For this purpose, the reaction is performed in a two-phase mixture of an aqueous base, preferably 30% sodium hydroxide solution, and a water-immiscible organic aprotic solvent. Suitable phase transfer catalysts are the compounds known to a person skilled in the art, but preferably tetraalkylammonium or tetraalkylphosphonium salts.

If it is desired to synthesize compounds of general Formula I wherein k, n, l and r=0 and R means a hydrogen atom, then it is possible to conduct the synthesis in analogy to the methods known from the literature, starting with the corresponding unsubstituted amino acid (e.g. phenylalanine).

However, if a series of analogous compounds is to be synthesized, then it is recommended to prepare the phenol derivatives described in DOS 3,710,730 and to reductively remove the phenol function in accordance with literature methods known to those skilled in the art. Above all, the reduction of aryl diethyl phosphates with titanium can be cited which can be performed in a very advantageous way also in the presence of ester groups [S. C. Welch et al., J. Org. Chem. 43: 4797—99 (1978) and literature cited therein]. In this procedure, the corresponding aryl diethyl phosphate is first formed from the phenolic educt by reaction with phosphoric acid diethyl ester chloride in a 70—100% yield, preferably by the use of sodium hydride as the base in a polar aprotic solvent. Subsequently, the reduction is performed with freshly prepared titanium metal. Preferably, anhydrous titanium(III) chloride is reduced by magnesium or potassium in anhydrous tetrahydrofuran under an inert gas for preparing highly active titanium.

The above-described diethyl phosphate is added to such a mixture and heated under reflux for 2–24 hours, preferably 6–16 hours. After the reaction is terminated, the mixture is optionally worked up by chromatography. It is also possible to employ the palladium-catalyzed reduction of the corresponding aryl triflates according to S. Cacchi et al., Tetr. Lett. 27: 5541—44 (1986).

The thus-obtained compounds of general Formula I' wherein X means a hydrogen atom represent complexing agents. They can be isolated and purified or can be converted, without isolation, into metal complexes of general Formula I with at least two of the substituents X meaning a metal ion equivalent.

The metal complexes of this invention can be produced in a way disclosed in Patent DE 3,401,052, by dissolving or suspending the metal oxide or a metal salt (e.g., the nitrate, acetate, carbonate, chloride or sulfate) of the element of atomic numbers 21—29, 42, 44 or 58—70 in water and/or a lower alcohol (such as methanol, ethanol or isopropanol) and reacting with a solution or suspension of the equivalent amount of the complex-forming acid of general Formula I' wherein X means a hydrogen atom, preferably at temperatures of between 40° and 100° C., and subsequently—if desired—substituting any present acidic hydrogen atoms of acid groups by cations of inorganic and/or organic bases, amino acids or amino acid amides.

Neutralization is herein effected with the aid of inorganic bases (for example, hydroxides, carbonates or bicarbonates) of, for example, sodium, potassium, lithium, magnesium or calcium and/or with the aid of organic bases, such as, inter alia, primary, secondary and tertiary amines, e.g., ethanolamine, morpholine, glucamine, N-methyl- and N,N-dimethylglucamine, as well as basic amino acids, such as, for example, lysine, arginine and ornithine.

In order to prepare the neutral complex compounds, it is possible, for example, to add to the acidic complex salts in an aqueous solution or suspension such an amount of the desired bases that the neutral point is reached. The resultant solution can subsequently be evaporated to dryness under vacuum. It is frequently advantageous to precipitate the thus-formed neutral salts by adding water-miscible solvents, such as, for example, lower alcohols (methanol, ethanol, isopropanol, and others), lower ketones (acetone and others), polar ethers (tetrahydrofuran, dioxane, 1,2-dimethoxyethane, and others), and to obtain in this way crystallized products which can be readily isolated and easily purified. It proved to be especially advantageous to add the desired base as early as during the complexing to the reaction mixture, thereby saving a process step.

If the acidic complex compounds contain several free acidic groups, then it is frequently expedient to prepare neutral mixed salts containing inorganic as well as organic cations as the counterions.

This can be done, for example, by reacting the complexing acid in an aqueous suspension or solution with the oxide or salt of the element yielding the central ion and with half the amount of an organic base needed for neutralization, isolating the thus-formed complex salt, purifying same if desired, and then combining same for complete neutralization with the required amount of inorganic base. The sequence or adding the bases can also be reversed.

The pharmaceuticals of this invention can be prepared in a likewise conventional way by suspending or dissolving the complex compounds according to the invention—optionally adding the additives customary in galenic pharmacy—in an aqueous medium and then optionally sterilizing the suspension or solution Suitable additives are, for example, physiologically acceptable buffers (e.g. tromethamine), small additions of complexing agents (such as, for example, diethylenetriaminepentaacetic acid) or, if necessary, electrolytes (such as, for example, sodium chloride) or, if necessary, antioxidants, e.g. ascorbic acid.

If, for enteral administration or other purposes, suspensions or solutions of the agents of this invention in water or a physiological saline solution are desirable, they are mixed with one or several auxiliary agent(s) customary in galenic pharmacy (for example methylcellulose, lactose, mannitol) and/or tenside(s), e.g. lecithins, "Tween", "Myrj" and/or flavoring substance(s) for taste improvement (e.g. ethereal oils).

In principle, it is also possible to prepare the pharmaceuticals of this invention even without isolation of the complex salts. In any event, special care must be directed toward effecting the chelate formation so that the salts and salt solutions according to this invention are practically devoid of toxically active metal ions that are not complexed.

This can be ensured, for example, wits; the aid of color indicators, such as xylenol orange, by control titrations during the manufacturing process. Consequently, the invention also relates to processes for preparing the complex compounds and their salts. The final safety feature resides in purification of the isolated complex salt.

The pharmaceutical agents of this invention can be administered to mammals, including humans, in a dose or 1 μmol/kg to 5 mmol/kg, preferably 10 μmol to 0.5 mmol/kg of the complex salt according to the invention. For intravenous injection, aqueous formulations are utilized with a concentration of 50 μmol/l to 2 mol/l, preferably 100 mmol/l to 1 mol/l. Rectal as well as oral administration is preferably performed with solutions of a concentration of 0.1 mmol/l to 100 mmol/l. The volumes administered are between 5 ml and 2 l, depending on the diagnostic problem.

The agents according to this invention meet the variegated prerequisites for suitability as contrast media. Thus, they are excellently suited, upon enteral or parenteral administration, to improve the information content of the image obtained with the aid of the NMR tomograph, by increasing the signal intensity. They show furthermore the high efficacy necessary for burdening the body with minimum amounts of foreign substances, and the good compatibility required for maintaining the non-invasive character of the tests.

The high water solubility and low osmolality of the agents according to this invention permits the production of highly concentrated solutions so that the volume load on the circulation is maintained within tolerable limits and dilution by body fluids is compensated. Furthermore, the agents of this invention exhibit not only a high stability in vitro but also a surprisingly high stability in vivo so that release or exchange of the—actually toxic—ions not covalently bound in the complexes takes place only extremely gradually within the time wherein the novel contrast media are again entirely eliminated.

The agents of this invention can also be utilized for radiation therapy. Thus, complexes of gadolinium are excellently suited due to the large capture cross section for neutron capture therapy. If the agent of this invention is intended for use in the version of radiation therapy proposed by R. L. Mills et al. [Nature, 336: 787 (1988)], then the central ion must be derived from a Mössbauer isotope, such as, for example, $^{57}$Fe or $^{151}$Eu.

When administered, the agents of this invention can also be given together with a suitable carrier, such as, for example, serum or physiological saline solution and/or together with a protein, such as, for example, human serum albumin. The dosage herein is dependent on the type of cellular disorder and on the properties of the metal complex utilized.

In certain aspects, this invention can exclude compounds and compositions wherein $Z^1$ is phenyl and $Z^2$ is H and aspects wherein, when —(O)$_r$—R is alkoxy, k, l, and q are simultaneously zero.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 22 005.2, filed Jun. 30, 1989, now DE 3922005, are hereby incorporated by reference.

EXAMPLE 1

(a) 3,6,9-Triaza-3,6,9-tris(tert-butoxycarbonylmethyl)-4-(4-methoxybenzyl) undecanedioic Acid Di-tert-butyl Diester At 0° C., 1.56 g (2 millimoles) of 3,6,9-triaza-3,6,9-tris (tert-butoxycarbonylmethyl)-4-(4-hydroxybenzyl) undecanedioic acid di-tert-butyl diester (Example 9f of DOS 3,710,730) is combined in tetrahydrofuran with 66 mg (2.2 mmol) of 80% strength sodium hydride. This mixtrure is combined with 0.31 g (2.2 mmol) of iodomethane and stirred for 30 minutes. Then the solution is combined with water, tetrahydrofuran is removed by distillation, and the aqueous emulsion is extracted with diethyl ether. The organic phase is washed with water, dried over $Na_2SO_4$, and concentrated.

Yield: 1.55 g (97.6%)

Calculated: C 63.53 H 9.01 N 5.2 Found: C 63.37 H 8.96 N 5.32

(b) 3,6,9-Triaza-3,6,9-tris(carboxymethyl)-4-(4-methoxybenzyl)undecanedioic Acid 1.27 g (1.6 mmol) of the tert-butyl ester described in Example 1(a) is dissolved in 25 ml of trifluoroacetic acid and stirred for one hour at room temperature. The solution is then combined with diethyl ether, the precipitate is suctioned off, washed with ether and dried at 40° C. under vacuum over phosphorus pentoxide. The crude product is dissolved in water and combined under agitation with active carbon. The mixture is filtered off from the carbon and lyophilized three times to remove residual trifluoroacetic acid.

Yield: 0.62 g (75.4%)

Calculated: C 51.46 H 6.09 N 8.18 Found: C 51.27 H 6.02 N 8.11

(c) Gadolinium Complex of 3,6,9-Triaza-3,6,9-tris (carboxymethyl)-4-(4-methoxybenzyl)undecanedioic Acid 513 mg (1 mmol) of the complexing acid described in Example 1(b) is dissolved in about 30 ml of water and combined at 80° C. with 181 mg (0.5 mmol) of $Gd_2O_3$. After 30 minutes, the almost clear solution is filtered and the filtrate freeze-dried.

Yield: 649 mg (97.2%) based on the anhydrous material

Calculated: C 39.57 H 4.23 N 6.29 Gd 23.55 Found: C 39.47 H 4.29 N 6.21 Gd 23.19

Disodium Salt of the Gadolinium Complex

The complex (500 mg, 0.75 mmol) obtained as described above is dissolved in 10 times the amount of water and combined by means of a microburette with 1.5 ml of a 1 N sodium hydroxide solution.

After freeze-drying, 533 mg of white crystals is obtained.

$T_1$ relaxation (1/mmol.sec) is in water 4.54±0.13 in plasma 6.89±0.17

Di-N-methyl-D-glucamine Salt of the Gadolinium Complex 3.34 g (5 mmol) of the gadolinium complex is combined in 40 ml of water in portions with 1.96 g (10 mmol) of N-methyl-D-glucamine under agitation. After the base has been completely dissolved, the product is freeze-dried There remains 5.55 g of a colorless crystalline compound.

H₂O content (Karl Fischer determination): 4.73%

(d) Europium Complex of 3,6,9-Triaza-3,6,9-tris(carboxymethyl)-4-(4-methoxybenzyl)undecanedioic Acid 5.13 g (10 mmol) of the complexing acid described in Example 1(b) is dissolved in about 30 ml of water and combined at 80° C. with 1.76 g (5 mmol) of $Eu_2O_3$. After 30 minutes, the almost clear solution is filtered and the filtrate freeze-dried.

Yield: 6.62 g

Analysis (based on anhydrous substance) Calculated: C 39.89 H 4.26 N 6.34 Eu 22.94 Found: C 39.71 H 4.38 N 6.17 Eu 22.58

Disodium Salt of the Europium Complex

The complex described above (497 mg, 0.75 mmol) is dissolved in 10 times the quantity of water and combined by means of a microburette with 1.5 ml of a 1 N sodium hydroxide solution. After freeze-drying, 540 mg of white crystals is obtained.

Di-N-methyl-D-glucamine Salt of the Europium Complex 3.31 g (5 mmol) of the europium complex is mixed in 40 ml of water in portions with 1.96 g (10 mmol) of N-methyl-D-glucamine under agitation. After the base has been completely dissolved, the mixture is freeze-dried. There remains 5.63 g of a colorless, crystalline compound.

(e) Iron(III) Complex of 3,6,9-Triaza-3,6,9-tris(carboxymethyl)-4-(4-methoxybenzyl)undecanedioic Acid 5.13 g (10 mmol) of the complexing acid disclosed in Example 1(b) is dissolved in about 30 ml of water and combined at 80° C. with 798 mg (5 mmol) of $Fe_2O_3$. After 30 minutes, the almost clear solution is filtered and the filtrate freeze-dried.

Yield: 5.66 g

Analysis (based on anhydrous substance): Calculated: C 46.66 H 4.98 N 7.42 Fe 9.86 Found: C 46.71 H 5.03 N 7.38 Fe 9.81

Disodium Salt of the Iron(III) Complex

The complex obtained as described above (425 mg, 0.75 mmol) is dissolved in 10 times the amount of water and combined by means of a microburette with 1.5 ml of a 1 N sodium hydroxide solution. After freeze-drying, 460 mg of white crystals is obtained.

Di-N-methyl-D-glucamine Salt of the Iron(III) Complex 2.83 g (5 mmol) of the iron(III) complex is combined in 40 ml of water in portions with 1.96 g (10 mmol) of N-methyl-D-glucamine under agitation. After the base has been completely dissolved, the solution is freeze-dried. There remains 4.83 g of a colorless, crystalline compound.

Analogously, with bismuth oxide, $Bi_2O_3$, the bismuth complex is obtained as the disodium salt and, respectively, as the di-N-methyl-D-glucamine salt.

EXAMPLE 2

(a) 3,6,9-Triaza-3,6,9-tris(tert-butoxycarbonylmethyl)-5-(4-methoxybenzyl)undecanedioic Acid Di-tert-butyl Ester In accordance with the directions given in Example 1(a), 3.9 g (5 mmol) of 3,6,9-triaza-3,6,9-tris(tert-butoxycarbonylmethyl)-5-(4-hydroxybenzyl)undecanedioic acid di-tert-butyl ester (Example 17d in DOS 3,710,730) is reacted to 3.61 g (91% of theory) of the title compound.

Calculated: C 63.53 H 9.01 N 5.29 Found: C 63.59 H 9.07 N 5.27

(b) 3,6,9-Triaza-3,6,9-tris(carboxymethyl)-5-(4-methoxybenzyl)undecanedioic Acid 3.18 g (4 mmol) of the tert-butyl ester described in Example 2(a) is treated in accordance with the directions set forth in Example 1(b) with trifluoroacetic acid and worked up, thus obtaining 1.62 g (79% of theory) of a colorless lyophilized product.

Calculated: C 51.46 H 6.09 N 8.18 Found: C 51.34 H 6.14 N 8.11

(c) Gadolinium Complex of 3,6,9-Triaza-3,6,9-tris(carboxymethyl)-5-(4-methoxybenzyl)undecanedioic Acid According to the directions in Example 1(c), 1.03 g (2 mmol) of the complex-forming acid described in Example 2(b) is complexed with $Gd_2O_3$, yielding 1.32 g (99% of theory) of a colorless lyophilized product.

Calculated: C 39.57 H 4.23 N 6.29 Gd 23.55 Found: C 39.51 H 4.19 N 6.25 Gd 23.61

The $T_1$ relaxation (1/mmol.sec) is in water 4.17±0.14 in plasma 6.61±0.18

EXAMPLE 3

(a) 3,6,9-Triaza-3,6,9-tris(tert-butoxycarbonylmethyl)-4-[4-(4-methoxybenzyloxy)benzyl]undecanedioic Acid Di-tert-butyl Ester At 0° C., 1.56 g (2 mmol) of 3,6,9-triaza-3,6,9-tris(tert-butoxycarbonylmethyl)-4-(4-hydroxybenzyl)undecanedioic acid di-tert-butyl ester (Example 9f of DOS 3,710,730) is combined in tetrahydrofuran with 66 mg (2.2 mmol) of 80% strength sodium hydride. To this mixture is added 0.3 ml (2.2 mmol) of 4-methoxybenzyl chloride and the mixture is stirred overnight. The solution is then combined with water, tetrahydrofuran is removed by distillation, and the aqueous emulsion is extracted with diethyl ether. The organic phase is washed with water, dried over $Na_2SO_4$, and concentrated. The resultant colorless oil is chromatographed on silica gel (ether/hexane 1:1).

Yield: 1.17 g (65% of theory) of a colorless oil.

Calculated: C 65.38 H 8.62 N 4.67 Found: C 65.29 H 8.65 N 4.59

(b) 3,6,9-Triaza-3,6,9-tris(carboxymethyl)-4-[4-(4-methoxybenzyloxy)benzyl]undecanedioic Acid 1.80 g (2 mmol) of the tert-butyl ester set forth in Example 3(a) is treated analogously to the directions given in Example 1(b) with trifluoroacetic acid and reacted to 905 mg (73% of theory) of colorless, flaky lyophilized product.

Calculated: C 56.21 H 6.02 N 6.78 Found: C 56.10 H 5.98 N 6.82

(c) Gadolinium Complex of 3,6,9-Triaza-3,6,9-tris(carboxymethyl)-4-[4-(4-methoxybenzyloxy)benzyl]-undecanedioic Acid Analogously to the directions given for Example 1(c), 620 mg (1 mmol) of the complexing acid described in Example 3(b) is complexed and worked up, yielding 758 mg (98% of theory).

Calculated: C 45.01 H 4.43 N 5.43 Gd 20.32 Found: C 44.93 H 4.49 N 5.37 Gd 20.18

The $T_1$ relaxation (1/mmol.sec) amounts to in water 4.23±0.16 in plasma 6.99±0.13

EXAMPLE 4

(a) Diethyl Phosphate of 3,6,9-Triaza-3,6,9-tris(tert-butoxycarbonylmethyl)-4-(4-hydroxybenzyl)-undecanedioic Acid Di-tert-butyl Ester 11.2 g (14.36 mmol) of the phenol disclosed in DOS 3,710,730 (Example 9f) is dissolved in 100 ml of absolute tetrahydrofuran (THF). To this mixture is adder 380 mg (15.8 mmol) of sodium hydride (prepared from 50% NaH in paraffin oil by washing three times with 10 ml of THF). After 30 minutes at room temperature, 2.60 g (15.0 mmol) of phosphoric acid diethyl ester chloride is added and the mixture stirred for 24 hours at room temperature.

The solution is diluted with 500 ml of ether and washed three times with 300 ml of 10% sodium hydroxide solution. After drying the organic phase over magnesium sulfate, the product is concentrated under vacuum and the residue purified by flash chromatography (eluent: ether/hexane= 1:1).

Yield: 11.97 g (91% of theory) of a pale-yellow oil.

Calculated: C 59.00 H 8.58 N 4.59 P 3.38 Found: C 58.88 H 8.63 N 4.63 P 3.30

(b) 3,6,9-Triaza-3,6,9-tris(tert-butoxycarbonylmethyl)-4-benzylundecanedioic Acid Di-tert-butyl Ester A mixture of 1.33 g (8.62 mmol) of anhydrous titanium (III) chloride and 1.02 g (26.09 mmol) of finely chopped potassium in 20 ml of tetrahydrofuran is heated under reflux in an argon atmosphere for one hour.

Within 15 minutes, a solution of 11.5 g (12.55 mmol) of the compound described in Example 4(a) in 50 ml of tetrahydrofuran is added dropwise to this mixture. Then the mixture is heated under reflux for 8 hours, cooled in an ice bath, 20 ml of methanol is gently added, then 100 ml of water is added, and the mixture is extracted three times with 200 ml of ether. The organic phases are dried over magnesium sulfate and concentrated under vacuum. The residue is chromatographed on silica gel (eluent: hexane/ether=2:1), thus obtaining 8.9 g (93% of theory) of the title compound as a colorless oil which crystallizes upon standing.

Calculated: C 64.46 H 9.10 N 5.50 Found: C 64.54 H 9.15 N 5.41

(c) 3,6,9-Triaza-3,6,9-tris(carboxymethyl)-4-benzylundecanedioic Acid

Analogously to the directions set forth in Example 1(b), 7.64 g (10 mmol) of the tert-butyl ester described in Example 4(b) is reacted to 4.01 g (83% of theory) of the title compound.

Calculated: C 52.17 H 6.05 N 8.69 Found: C 52.23 H 5.99 N 8.73

(d) Gadolinium Complex of 3,6,9-Triaza-3,6,9-tris(carboxymethyl)-4-benzylundecanedioic Acid 2.42 g (5 mmol) of the complex-forming acid described in Example 4(c) is reacted analogously to the directions given in Example 1(c) to 3.14 g (98.5% of theory) of the title compound, obtaining the gadolinium complex as a colorless, flaky lyophilized product.

Calculated: C 39.55 H 4.11 N 6.59 Gd 24.66 Found: C 39.47 H 4.19 N 6.52 Gd 24.88

The $T_1$ relaxation (1/mmol.sec) is in water 4.54±0.13 in plasma 6.89±0.17

Ytterbium Complex of 3,6,9-Triaza-3,6,9-tris(carboxymethyl)-4-benzylundecanedioic Acid Analogously to the directions for preparing the gadolinium complex, the corresponding ytterbium complex is obtained by using $Yb_2O_3$ in place of $Gd_2O_3$.

EXAMPLE 5

(a) 3,6,9-Triaza-3,6,9-tris(tert-butoxycarbonylmethyl)-4-benzyloxymethylundecanedioic Acid Di-tert-butyl Ester Within 30 minutes, 7.2 ml (60 mmol) of benzyl bromide is added dropwise at room temperature to a thoroughly stirred suspension of 14.1 g (20 mmol) of 4-hydroxymethyl-3,6,9-triaza-3,6,9-tris(tert-butoxycarbonylmethyl) undecanedioic di-tert-butyl diester described in DOS 3,710, 730 (Example 37d) and 0.3 g of tetrabutylammonium hydrogen sulfate in 200 ml of dichloromethane/200 ml of 30% strength sodium hydroxide solution, and the mixture is then agitated for 8 hours.

400 ml of water is added to this suspension; the organic phase is separated and the aqueous phase extracted twice with respectively 150 ml of dichloromethane. After drying the combined organic phases over magnesium sulfate, the product is chromatographed on silica gel (ether/hexane= 1:1), thus obtaining 13.0 g (82% of theory) of the title compound as a colorless oil.

Calculated: C 63.53 H 9.01 N 5.29 Found: C 63.42 H 9.07 N 5.21

(b) 3,6,9-Triaza-3,6,9-tris(carboxymethyl)-4-benzyloxymethylundecanedioic Acid

Analogously to the directions given for Example 1(b), 7.94 g (10 mmol) of the tert-butyl ester set forth in Example 5(a) is reacted with trifluoroacetic acid to 4.06 g (79% of theory) of the title compound.

Calculated: C 51.46 H 6.09 N 8.18 Found: C 51.51 H 6.06 N 8.12

(c) Gadolinium Complex of 3,6,9-Triaza-3,6,9-tris(carboxymethyl)-4-benzyloxymethylundecanedioic Acid In analogy to the directions in Example 1(c), 2.57 g (5 mmol) of the complexing acid described in Example 5(b) is reacted to 3.30 g (98.9% of theory) of the title compound, yielding a colorless, flaky solid.

Calculated: C 39.57 H 4.23 N 6.29 Gd 23.55 Found: C 39.51 H 4.26 N 6.35 Gd 23.27

The $T_1$ relaxation (1/mmol.sec) is in water 4.39±0.12 in plasma 6.31±0.15

EXAMPLE 6

(a) 3,6,9-Triaza-3,6,9-tris(tert-butoxycarbonylmethyl)-4-(4-carboxymethoxybenzyl)undecanedioic Acid Bis(tert-butyl) Ester At 0° C., 23.40 g (30 mmol) of 3,6,9-triaza-3,6,9-tris(tert-butoxycarbonylmethyl)-4-(4-hydroxybenzyl)undecanedioic acid di-tert-butyl ester (Example 9f of DOS 3,710,730) is combined in tetrahydrofuran with 2.7 g (90 mmol) of 80% strength sodium hydride. To this mixture is dropped 6.25 g (45 mmol) of bromoacetic acid in tetrahydrofuran, and the mixture is stirred for one hour at 0° C. and overnight at room temperature.

The solution is then combined with water, tetrahydrofuran is removed by distillation, and the aqueous phase is extracted with ethyl acetate. The organic phase is dried over sodium sulfate and concentrated.

The residue is chromatographed on silica gel in an eluent mixture of dioxane/methanol/triethylamine (15:4:1); the combined fractions are concentrated and divided between ethyl acetate and 1 N citric acid. The organic phase is then dried over sodium sulfate and concentrated, thus obtaining 21.8 g (87% of theory) as a colorless oil.

Calculated: C 61.63 H 8.54 N 5.01 Found: C 61.62 H 8.62 N 4.95

(b) 3,6,9-Triaza-3,6,9-tris(carboxymethyl)-4-(4-carboxymethoxybenzyl)undecanedioic Acid Analogously to the directions given for Example 1(b), 21.0 g (25 mmol) of the tert-butyl ester described in Example 6(a) is reacted to 11.0 g (78.9% of theory) of the title compound.

Calculated: C 49.55 H 5.60 N 7.54 Found: C 49.31 H 5.51 N 7.47

(c) Gadolinium Complex of 3,6,9-Triaza-3,6,9-tris(carboxymethyl)-4-(4-carboxymethoxybenzyl) undecanedioic Acid 5.57 g (10 mmol) of the complex-forming acid described in Example 6(b) is reacted analogously to the directions set forth in Example 1(c) to yield 7.01 g (98.5% of theory) of the title compound.

Calculated: C 38.81 H 3.96 N 5.90 Gd 22.09 Found: C 38.75 H 3.89 N 5.97 Gd 21.93

The $T_1$ relaxation (1/mmol.sec) is in water 5.00±0.01 in plasma 7.10±0.08

EXAMPLE 7

Preparation of a Solution of the Sodium Salt of the Gadolinium(III) Complex of 3,6,9-Triaza-3,6,9-tris(carboxymethyl)-4-benzyloxymethylundecanedioic Acid 6.68 g (10 mmol) of the gadolinium complex obtained according to Example 5(c) is dissolved in 70 ml of water pro injectione (p.i.) and combined dropwise with 1 N sodium hydroxide solution until a pH of 7.2 has been reached. After adding 0.02 g of tromethamine, the mixture is filled up to 100 ml with water p.i.; the solution is dispensed into bottles and heat-sterilized.

EXAMPLE 8

(a) 3,6,9-Triaza-3,6,9-tris(tert-butoxycarbonylmethyl)-4-(4-ethoxybenzyl) undecanedioic Acid Di-tert-butyl Diester At 0° C., 5.85 g (7.5 mmol) of 3,6,9-triaza-3,6,9-tris(tert-butoxycarbonylmethyl)-4-(4-hydroxybenzyl)undecanedioic acid di-tert-butyl diester (Example 9f of DOS 3,710,730) is combined in 100 ml of tetrahydrofuran with 0.30 g (10 mmol) of 80% strength sodium hydride. To this mixture is added 1.56 g (10 mmol) of iodoethane and the mixture is stirred for 3 hours. Then the solution is combined with water, tetrahydrofuran is distilled off, and the aqueous emulsion is extracted with diethyl ether. The crude product obtained after drying over sodium sulfate and concentration of the solvent is chromatographed on silica gel (system: hexane/ether/triethylamine 70:30:5).

Yield: 4.0 g (66%)

Analysis (based on anhydrous material): Calculated: C 63.91 H 9.11 N 5.20 Found: C 63.67 H 9.05 N 5.28

(b) 3,6,9-Triaza-3,6,9-tris(carboxymethyl)-4-(4-ethoxybenzyl)undecanedioic Acid 3.64 g (4.5 mmol) of the tert-butyl ester disclosed in Example 8(a) is dissolved in 25 ml of trifluoroacetic acid, stirred for one hour at room temperature, and worked up analogously to Example 1(b).

Yield: 1.2 g (50.6%)

Analysis (based on anhydrous substance): Calculated: C 52.36 H 6.13 N 7.97 Found: C 52.21 H 6.39 N 7.84

(c) Disodium Salt of the Gadolinium Complex of 3,6,9-Triaza-3,6,9-tris(carboxymethyl)-4-(4-ethoxybenzyl)undecanedioic Acid 528 mg (1 mmol) of the complex-forming acid described in the preceding example is dissolved in 40 ml of water and complexed at 80° C. with 181 mg (0.5 mmol) of $Gd_2O_3$. Then the mixture is neutralized with 2 ml of 1 N NaOH, stirred with activated carbon, filtered, and the filtrate is freeze-dried.

Yield: 700 mg (96.5%)

Analysis (based on anhydrous material): Calculated: C 38.06 H 3.89 Gd 21.67 N 5.79 Na 6.34 Found: C 37.91 H 3.99 Gd 21.30 N 5.69 Na 6.57

The $T_1$ relaxation (1/mmol.sec) is in water 5.33±0.13 in plasma 8.69±0.53

Analogously, the corresponding europium complex is obtained with europium oxide, $Eu_2O_3$.

Calculated: C 38.34 H 3.92 Eu 21.09 N 5.83 Na 6.38 Found: C 38.20 H 4.01 Eu 20.87 N 5.79 Na 6.49

With iron oxide, $Fe_2O_3$, the corresponding iron complex is obtained analogously:

Calculated: C 44.25 H 4.52 Fe 8.95 N 6.73 Na 7.37 Found: C 44.17 H 4.59 Fe 8.52 N 6.81 Na 7.49

EXAMPLE 9

(a) 3,6,9-Triaza-3,6,9-tris(tert-butoxycarbonylmethyl)-4-(4-butoxybenzyl) undecanedioic Acid Di-tert-butyl Diester Analogously to Example 8(a), 5.85 g (7.5 mmol) of 3,6,9-triaza-3,6,9-tris(tert-butoxycarbonylmethyl)-4-(4-hydroxybenzyl)undecanedioic acid di-tert-butyl diester (Example 9f of DOS 3,710,730) is reacted with 1.84 g (10 mmol) of 1-iodobutane and worked up as described therein.

Yield: 4.1 g (65.4%)

Analysis (based on anhydrous compound): Calculated: C 64.64 H 9.28 N 5.03 Found: C 64.82 H 9.37 N 4.96.

(b) 3,6,9-Triaza-3,6,9-tris(carboxymethyl)-4-(4-butoxybenzyl)undecanedioic Acid 3.34 g (4 mmol) of the tert-butyl ester described in Example 9(a) is dissolved in 20 ml of trifluoroacetic acid, stirred for one hour at room temperature, and worked up analogously to Example 1(b).

Yield: 1.36 g (61.0%)

Analysis (based on anhydrous material): Calculated: C 54.04 H 6.71 N 7.57 Found: C 53.88 H 6.63 N 7.41

(c) Disodium Salt of the Gadolinium Complex of 3,6,9-Triaza-3,6,9-tris(carboxymethyl)-4-(4-butoxybenzyl)undecanedioic Acid 556 mg (1 mmol) of the complexing acid described in the preceding example is combined with 40 ml of water and complexed at 80° C. with 181 g (0.5 mmol) of $Gd_2O_3$. The mixture is then neutralized with 2 ml of 1 N NaOH, stirred with activated carbon, filtered, and the filtrate freeze-dried.

Yield: 711 mg (94.3%)

Analysis (based on anhydrous material): Calculated: C 39.83 H 4.28 Gd 20.86 N 5.58 Na 6.10 Found: C 39.61 H 4.35 Gd 20.51 N 5.49 Na 6.17

The $T_1$ relaxation (1/mmol.sec) is in water 5.80±0.26 in plasma 14.20±0.98

Analogously, with the use of europium oxide, $Eu_2O_3$, the corresponding europium complex is obtained:

Calculated: C 40.11 H 4.31 Eu 20.30 N 5.61 Na 6.14 Found: C 39.97 H 4.39 Eu 20.02 N 5.72 Na 6.25

With iron oxide, $Fe_2O_3$ the corresponding iron complex is analogously obtained:

Calculated: C 46.03 H 4.94 Fe 8.56 N 6.44 Na 7.05 Found: C 45.88 H 5.03 Fe 8.30 N 6.50 Na 7.11

EXAMPLE 10

(a) 3,6,9-Triaza-3,6,9-tris(tert-butoxycarbonylmethyl)-4-(4-benzyloxybenzyl) undecanedioic Acid Di-tert-butyl Diester Analogously to Example 8(a), 5.85 g (7.5 mmol) of 3,6,9-triaza-3,6,9-tris(tert-butoxycarbonylmethyl)-4-(4-hydroxybenzyl)undecanedioic acid di-tert-butyl diester (Example 9f of DOS 3,710,730) is reacted with 1.71 g (10 mmol) of benzyl bromide and worked up as described therein.

Yield: 4.9 g (75.1%)

Analysis (based on anhydrous substance): Calculated: C 66.25 H 8.69 N 4.83 Found: C 66.14 H 8.77 N 4.83

(b) 3,6,9-Triaza-3,6,9-tris(carboxymethyl)-4-(4-benzyloxybenzyl)undecanedioic Acid 3.48 g (4 mmol) of the tert-butyl ester disclosed in Example 10(a) is dissolved in 20 ml of trifluoroacetic acid, stirred for one hour at room temperature, and worked up analogously to Example 1(b).

Yield: 1.33 g (56.5%)

Analysis (based on anhydrous material): Calculated: C 57.04 H 5.98 N 7.13 Found: C 56.89 H 6.03 N 7.21

(c) Disodium Salt of the Gadolinium Complex of 3,6,9-Triaza-3,6,9-tris(carboxymethyl)-4-(4-benzyloxybenzyl)undecanedioic Acid 590 mg (1 mmol) of the complexing acid described in the preceding example is combined with 40 ml of water and 1 ml of 1 N NaOH and complexed at 80° C. with 181 mg (0.5 mmol) of $Gd_2O_3$. Then the mixture is neutralized furthermore with 1 ml of 1 N NaOH, stirred with active carbon, filtered, and the filtrate freeze-dried.

Yield: 703 mg (89.2%)

Analysis (based on anhydrous material): Calculated: C 42.69 H 3.84 Gd 19.96 N 5.33 Na 5.84 Found: C 42.63 H 3.91 Gd 19.57 N 5.26 Na 5.99

The $T_1$ relaxation (1/mmol.sec) is in water 5.81±0.11 in plasma 16.35±1.01

The corresponding europium complex is obtained analogously with europium oxide, $Eu_2O_3$:

Calculated: C 42.98 H 3.86 Eu 19.42 N 5.37 Na 5.88 Found: C 43.10 H 3.91 Eu 19.13 N 5.27 Na 5.99

With iron oxide, $Fe_2O_3$, the corresponding iron complex is obtained analogously:

Calculated: C 48.99 H 4.41 Fe 8.14 N 6.12 Na 6.70 Found: C 48.73 H 4.57 Fe 8.29 N 6.03 Na 6.85

EXAMPLE 11 a) 4-Nitro-N-benzyloxycarbonyl-DL-phenylglycine-(2-aminoethyl)-amide-hydrochloride 588.5 g (3 mol) of 4-nitro-DL-phenylglycine, produced according to J. Biochem. (Tokyo) 88(6), 1773, is suspended in 2.5 liters of ethanol. 713.8 g (6 mol) of thionyl chloride is instilled under ice cooling within 90 minutes, refluxed for two hours, and the resulting solution is evaporated to dryness in a vacuum. The residue is dissolved in 5 liters of water, mixed with 5 liters of diethyl ether and brought to pH 8.5 with 1.5 liters of a 1.5 m-sodium carbonate solution. Then, 511.8 g (3 mol) of chloroformic acid benzyl ester and 1.8 liters of 1.5 m-sodium carbonate solution are instilled simultaneously with intensive stirring, so that the pH of the mixture is between 8.2 and 8.6. It is allowed to stir for two hours at room temperature, the organic phase is separated, it is washed neutral with water, dried on sodium sulfate and the filtered solution is evaporated to dryness. The residue is dissolved in 2 liters of methanol, and the solution is instilled slowly in 3.5 liters of ethylenediamine with intensive stirring. It is allowed to stir for 24 hours, evaporates to dryness in a vacuum, the residue is dissolved in 2 liters of hot methanol and the solution is mixed by instillation under cooling with conc. hydrochloric acid until permanent turbidity. It is allowed to crystallize in the ice bath for 24 hours, the precipitate is suctioned off, it is washed with a little ice-cold methanol and it is dried in a vacuum at 40° C.

1022.3 g (90% of theory) of the title compound is obtained as a yellow powder with an uncharacteristic decomposition point.

Analysis: C 52.88 H 5.18 N 13.70 (calculated) 52.61 5.24 13.77 (found)

b) 1,5-Diamino-3-aza-1-(4-nitrophenyl)-pentane 255.5 g (0.625 mol) of the compound obtained under a) is suspended in 650 ml of a solution of hydrobromic acid in glacial acetic acid. It is allowed to stir for 30 minutes at room temperature and the solution is mixed with diethyl ether until permanent turbidity. After stirring overnight, the precipitated hydrobromide is suctioned off, dried and dissolved in 2 liters of water. After treatment with 1.25 liters of AMBERLITE IRA 410 ion exchange material, the filtered solution is evaporated to dryness and dehydrated by codistillation with toluene. The residue is dissolved in 500 ml of tetrahydrofuran and again concentrated by evaporation. Then, 4.5 liters of a one-molar diborane-tetrahydrofuran complex solution in tetrahydrofuran (ALDRICH) is added and refluxed for 72 hours. After cooling off the solution, 500 ml of methanol is carefully instilled and saturated under ice cooling with hydrochloric acid. It is allowed to stir for four more hours, the precipitate is suctioned off and dried in a vacuum after washing with tetrahydrofuran at room temperature. 170.9 g of the title compound is obtained as trihydrochloride of equivalent weight 113.4 (calculated: 111.2).

c) 3,6,9-Triaza-3,6,9-tris(carboxymethyl)-4-(4-nitrophenyl)-undecanedioic Acid 58.4 g (175 mmol) of the compound obtained under b) is dissolved in 630 ml of water and 420 ml of a 10 molar potassium hydroxide solution, mixed with 1.1 liters of tetrahydrofuran and, after the addition of 165.4 g (1.75 mol) of chloroacetic acid, stirred for 72 hours at 50° C. It is cooled off to room temperature, the aqueous phase is separated, neutralized with conc. hydrochloric acid, and the solution is evaporated to dryness in a vacuum. The residue is dehydrated by codistillation with toluene, 2 liters of ethanol is added and 312.3 g of thionyl chloride is instilled under ice cooling. It is refluxed for five hours, evaporated to dryness in a vacuum and the residue is mixed with 2 liters of ethyl acetate and 4 liters of a one-molar sodium bicarbonate solution. It is allowed to stir for two hours, the organic phase is separated, it is washed with water, dried on sodium sulfate, filtered and evaporated to dryness in a vacuum. The remaining yellow oil is the pentaethyl ester of the title compound. For saponification, 150 ml of tetrahydrofuran an 150 ml (750 mmol) of 5 n sodium hydroxide solution are added and allowed to stir for four hours at room temperature. The aqueous phase is separated, filtered several times on activated carbon and acidified with 50% by volume of sulfuric acid. It is allowed to stir for 24 hours in an ice bath, the precipitate is suctioned off, it is washed with ice water and dried in a vacuum at 50° C. 55.8 g (62% of theory) of the title compound is obtained as a white powder with a decomposition point above 250° C.

Analysis: C 46.69 H 5.09 N 10.89 (calculated) 46.48 5.20 11.01 (found)

d) 3,6,9-Triaza-3,6,9-tris(carboxymethyl)-4-(hydroxyphenyl)-undecanedioic Acid 51.4 g (0.1 mol) of the compound obtained under c) is suspended in 500 ml of water and brought into solution by adding conc. sodium hydroxide solution. The solution is mixed in an autoclave with 5 g of palladium-carbon catalyst (10% Pd) and saturated with hydrogen gas. After completion of the hydrogenation, it is suctioned off from the catalyst, the solution is filtered on activated carbon and mixed with 15 ml of glacial acetic acid. Then, a solution of 11 g (150 mmol) of sodium nitrite in 50 ml of water and 50 ml of glacial acetic acid is simultaneously instilled in the ice bath with stirring, so that an inner temperature of 5° C. is not exceeded. It is allowed to stir for two hours at 5° C., then for two more hours at room temperature, 50 ml of nitric acid (1:3) is added by instillation and heated for three hours to 50° C. After cooling of and stirring in the ice bath overnight, the precipitate is suctioned off, washed with water and recrystallized from 90% ethanol. 29.1 g (60% of theory) of the title compound is obtained as a white powder with a decomposition point above 250° C.

Analysis: C 49.48 H 5.61 N 8.66 49.52 5.80 8.62 e) 3,6,9-Triaza-3,6,9-tris(carboxymethyl)-4-(4-ethoxyphenyl)-undecanedioic Acid 4.85 g (10 mmol) of the compound obtained under d) is dissolved in 20 ml of dimethyl formamide. After cooling off in the ice bath, 300 mg (10 mmol) of 80% sodium hydride and then 1.56 g (10 mmol) of iodine ethane are carefully added and allowed to stir at room temperature overnight. It is heated for two hours to 40° C., 5 ml of water is carefully instilled and the solution is evaporated to dryness in a vacuum. The residue is stirred up with 100 ml of diethyl ether overnight, suctioned off and suspended in 20 ml of 2 n hydrochloric acid. It is allowed to stir for one hour, again suctioned off, washed with water and dried in a vacuum at 40° C. [Several words illegible] title compound is obtained as a white powder with an uncharacteristic decomposition point.

Analysis: C 51 46 H 6.08 N 8.18 51.33 6.17 8.13 f) Disodium Salt of the Gadolinium Complex of 3,6,9-triaza-3,6,9-tris(carboxymethyl)-4-(4-ethoxyphenyl)-undecanedioic Acid 5.0 g of the compound obtained under e) is reacted in 30 ml of water with 1812 mg (5 mmol) of gadolinium oxide at 80° C. within one hour. The solution is ultrafiltered and freeze-dried. The title compound is obtained in quantitative yield with a gadolinium content of 22.1% (relative to the anhydrous substance).

Melting point: greater than 300° C.

EXAMPLE 12

Analogously, as described in example 11, starting from 2-amino-4-(4-nitrophenyl)-butyric acid, the complexes, according to the invention, of 3,6,9-triaza-3,6,9-tris (carboxymethyl)-4-(4-ethoxyphenylethyl)-undecanedioic acid are obtained.

Melting point: greater than 300° C.

EXAMPLES FOR IN VIVO NMR DIAGNOSTICS

Example 1

Images were obtained at various times after administration of the disodium salt of the gadolinium complex of Example 1(c) to rats with the aid of an NMR tomograph by General Electric, specifically developed for animal experimental research.

Spin echo scans were made with the NMR tomograph (CSI 2 T) at 2 tesla (TR time of 400 ms and TE time of 20 ms). The layer thickness of this $T_1$-weighted imaging sequence was 3 mm; the image matrix was 128×128.

The contrast medium was administered intravenously into a caudal vein of a male hairless rat (Lew/Mol) weighing 190 g, in a dose of 0.06 mmol/kg The animal had a Brown Pearce tumor in the thigh and was anesthetized for the study by means of an intramuscular administration of "Ketavet"/"Rompun".

Various dark structures are visible in the abdomen in the coronary blank scan (baseline, No. 1). No differentiation was possible between intestinal lumen and stomach.

One minute after administration (No. 2), the first enhancement is already apparent in the urinary bladder. A strong increase in contrast is visible in the stomach 45 minutes after injection (No. 3). A good visualization of the tumor (at the level of the reference tube) of the urinary bladder, and of the stomach can be observed 60 minutes after injection (No. 4). Moreover, contrasting of the intestine can likewise be observed. This makes it possible to distinguish among intestinal loops, fat, as well as lymphatic nodes (lymphomas). Contrasting of the renal pelvis is also striking;

this image can be even more improved 65 minutes after injection in a somewhat different layer (No 5). 180 minutes after injection, the contrast enhancement is likewise clearly recognizable in an axial scan in the zone of the liver. This makes it possible to differentiate among the stomach, the liver, the duodenum, and the pancreas.

Example 2

The test animals were female rats of the strain Lew/Mol weighing 160–180 g. Prior to imaging, the animals were anesthetized ("Rompun"+"Ketavet") and provided with a catheter in the caudal vein to administer the contrast medium. Imaging took place in an MRI experimental device by General Electric (field strength 2 tesla). First of all, the images (7, 9, 11) were made without contrast medium with a $T_1$-weighted spin echo sequence (TR=400 msec, TE=20 msec, axial section plane, layer thickness 3 mm). The liver appears in each case with the normal signal intensity; the stomach is darker in tendency than the liver. In case of animal 1, the stomach exhibits, in part, a rather high signal intensity. This is due to feed residues, the feed containing manganese in relatively high concentrations (at the time of the test, the animals had been fasting for 6 hours). Animal 3 had been implanted with an osteogenic sarcoma three weeks previously; this sarcoma was of equal contrast in the blank image and could not be defined. The administration of contrast medium took place via the venous catheter with a dose of 0.1 mmol Gd/kg (concentration of the solutions 0.05 mmol Gd/ml in 0.9% NaCl) for all 3 compounds.

A marked enhancement of the liver can be found for all 3 compounds after 90 minutes [Example 8(c)] and, respectively, after 60 minutes have elapsed upon administration [Example 9(c); FIG. 12, Example 10(c)]; this is due to uptake by the hepatocytes and cannot be observed at this point in time after administration with the contrast medium for NMR tomography, "Magnevist", heretofore the sole contrast medium available on the market. In case of animal 3 [Example 10(c)], the tumor is now additionally clearly visible, which has not absorbed the contrast medium at all, or only to a lesser proportion.

Furthermore, all compounds—most strongly in case of Example 10(c), least in case of Example 8(c)—show great enhancement of the stomch. This offers additional diagnostic possibilities in view of an improved distinction of liver and stomach.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of enhancing an NMR image comprising administering to a patient a compound of the formula

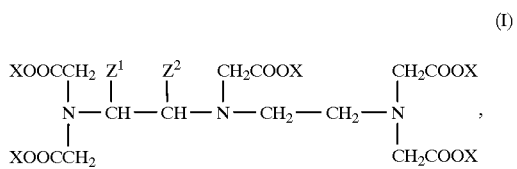

(I)

wherein
one of $Z^1$ and $Z^2$ is H and the other is

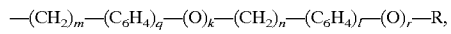

$-(CH_2)_m-(C_6H_4)_q-(O)_k-(CH_2)_n-(C_6H_4)_r-(O)_r-R$, wherein
m and n, independently, are each 0–20,
k, l, q and r are each, independently, 0 or 1,
R is H, $C_1$–$C_6$-alkyl, $OR^1$-substituted $C_1$–$C_6$-alkyl or $CH_2COOR^1$,
$R^1$ is H, $C_1$–$C_6$-alkyl or benzyl; and
X is, in each case, a hydrogen atom or a metal ion equivalent of an element of atomic number 21–29, 42, 44 or 58–70;
with the provisos that:
at least two X groups represent a metal ion equivalent of atomic number 21–29, 42, 44 or 58–70;
when n and l are each 0, then k and r are not each simultaneously 1;
$-(O)_r-R$ is not —OH;
$Z^1$ and $Z^2$ are not —$C_6H_5$, —$CH_2$—$C_6H_5$, —$CH_2$—$C_6H_4$—O—$CH_2$—$COOCH_2C_6H_5$ or —$CH_2$—$C_6H_4$—O—$(CH_2)_5$—$COOCH_2C_6H_5$; and
at least one of q and l is 1;
or a physiologically acceptable salt thereof with an inorganic and/or organic base, an amino acid or an amino acid amide.

2. A method of claim 1, wherein $Z^1$ is hydrogen and $Z^2$ is $-(CH_2)_m-(C_6H_4)_q-(O)_k-(CH_2)_n-(C_6H_4)_r-(O)_r-R$, which is not hydrogen.

3. A method of claim 1, wherein $Z^2$ is hydrogen and $Z^1$ is $-(CH_2)_m-(C_6H_4)_q-(O)_k-(CH_2)_n-(C_6H_4)_r-(O)_r-R$, which is not hydrogen.

4. A method of claim 1, wherein $Z^1$ is —$CH_2$—$C_6H_4$—$OCH_3$, —$CH_2$—$C_6H_4$—O—$CH_2$—$C_6H_4$—$OCH_3$, —$CH_2$—O—$CH_2$—$C_6H_5$, —$CH_2$—$C_6H_4$—O—$CH_2$—COOH, —$CH_2$—$C_6H_4$—$OC_2H_5$, —$CH_2$—$C_6H_4$—$OC_4H_9$ or —$CH_2$—$C_6H_4$—O—$CH_2$—$C_6H_5$.

5. A method of claim 4, wherein $Z^1$ is —$CH_2$—$C_6H_4$—$OCH_3$, —$CH_2$—$C_6H_4$—O—$CH_2$—$C_6H_4$—$OCH_3$, —$CH_2$—O—$CH_2$—$C_6H_5$ or —$CH_2$—$C_6H_4$—O—$CH_2$—COOH.

6. A method of claim 1, wherein $Z^2$ is —$CH_2$—$C_6H_4$—$OCH_3$, —$CH_2$—$C_6H_4$—O—$CH_2$—$C_6H_4$—$OCH_3$, —$CH_2$—O—$CH_2$—$C_6H_5$, —$CH_2$—$C_6H_4$—O—$CH_2$—COOH, —$CH_2$—$C_6H_4$—$OC_2H_5$, —$CH_2$—$C_6H_4$—$OC_4H_9$ or —$CH_2$—$C_6H_4$—O—$CH_2$—$C_6H_5$.

7. A method of claim 6, wherein $Z^2$ is —$CH_2$—$C_6H_4$—$OCH_3$, —$CH_2$—$C_6H_4$—O—$CH_2$—$C_6H_4$—$OCH_3$, —$CH_2$—O—$CH_2$—$C_6H_5$ or —$CH_2$—$C_6H_4$—O—$CH_2$—COOH.

8. A method of claim 1, wherein at least three X groups represent a Gd ion.

9. A method of claim 4, wherein at least three X groups represent a Gd ion.

10. A method of claim 6, wherein at least three X groups represent a Gd ion.

11. A method of claim 1, wherein said compound is:
gadolinium complex of 3,6,9-triaza-3,6,9-tris(carboxymethyl)-4-(4-methoxybenzyl)undecanedioic acid or a physiologically acceptable salt thereof;
europium complex of 3,6,9-triaza-3,6,9-tris(carboxymethyl)-4-(4-methoxybenzyl)undecanedioic acid or a physiologically acceptable salt thereof;
iron(III) complex of 3,6,9-triaza-3,6,9-tris(carboxymethyl)-4-(4-methoxybenzyl)undecanedioic acid or a physiologically acceptable salt thereof;
gadolinium complex of 3,6,9-triaza-3,6,9-tris(carboxymethyl)-5-(4-methoxybenzyl)undecanedioic acid or a physiologically acceptable salt thereof;
gadolinium complex of 3,6,9-triaza-3,6,9-tris(carboxymethyl)-4-[4-(4-methoxybenzyloxy)benzyl]undecanedioic acid or a physiologically acceptable salt thereof;
gadolinium complex of 3,6,9-triaza-3,6,9-tris(carboxymethyl)-4-benzyloxymethylundecanedioic acid or a physiologically acceptable salt thereof;
gadolinium complex of 3,6,9-triaza-3,6,9-tris(carboxymethyl)-4-(4-carboxymethoxybenzyl)undecanedioic acid or a physiologically acceptable salt thereof;
gadolinium complex of 3,6,9-triaza-3,6,9-tris(carboxymethyl)-4-(4-ethoxybenzyl)undecanedioic acid or a physiologically acceptable salt thereof;
europium complex of 3,6,9-triaza-3,6,9-tris(carboxymethyl)-4-(4-ethoxybenzyl)undecanedioic acid or a physiologically acceptable salt thereof;
iron complex of 3,6,9-triaza-3,6,9-tris(carboxymethyl)-4-(4-ethoxybenzyl)undecanedioic acid or a physiologically acceptable salt thereof;
gadolinium complex of 3,6,9-triaza-3,6,9-tris(carboxymethyl)-4-(4-butoxybenzyl)undecanedioic acid or a physiologically acceptable salt thereof;
europium complex of 3,6,9-triaza-3,6,9-tris(carboxymethyl)-4-(4-butoxybenzyl)undecanedioic acid or a physiologically acceptable salt thereof;
iron complex of 3,6,9-triaza-3,6,9-tris(carboxymethyl)4-(4-butoxybenzyl)undecanedioic acid or a physiologically acceptable salt thereof;
gadolinium complex of 3,6,9-triaza-3,6,9-tris(carboxymethyl)-4-(4-benzyloxybenzyl)undecanedioic acid or a physiologically acceptable salt thereof;
europium complex of 3,6,9-triaza-3,6,9-tris(carboxymethyl)-4-(4-benzyloxybenzyl)undecanedioic acid or a physiologically acceptable salt thereof;
iron complex of 3,6,9-triaza-3,6,9-tris(carboxymethyl)-4-(4-benzyloxybenzyl)undecanedioic acid or a physiologically acceptable salt thereof.

12. A method of claim 1, wherein the renal system is imaged.

13. A method of claim 1 wherein the hepatobiliary system is imaged.

14. A method according to claim 1, wherein two of the X groups represent manganese(II), iron(II), cobalt(II) or copper(II); or three of the X groups represent chromium(III), praseodymium(III), neodymium(III), samarium(III), ytterbium(III), gadolinium(III), terbium(III), dysprosium(III), holmium(III), erbium(III), or iron(III).

15. A method to claim 1, wherein $Z^1$ is —$C_6H_4$—O—$C_2H_5$ or —$C_2H_4$—$C_6H_4$—O—$C_2H_5$.

16. A method according to claim 1, wherein said compound is gadolinium complex of 3,6,9-triaza-3,6,9-tris(carboxymethyl)-4-(4-ethoxyphenyl)undecanedioic acid or a physiologically acceptable salt thereof.

17. A method according to claim 1, wherein said compound is a complex of 3,6,9-triaza-3,6,9-tris(carboxymethyl)-4-(4-ethoxyphenylethyl)undecanedioic acid and a metal ion of atomic number 21–29, 42, 44 or 57–83, or a physiologically acceptable salt thereof.

18. A method according to claim 1, wherein R is $C_{1-6}$-alkyl or $C_{1-6}$-alkyl substituted by —$OR^1$.

19. A method according to claim 1, wherein one of $Z^1$ and $Z^2$ is —$CH_2$—$C_6H_4$—O—$(CH_2)_n$—$(C_6H_4)_l$—$(O)_r$—R.

20. A method according to claim 1, wherein one of $Z^1$ and $Z^2$ is —$(CH_2)$—$C_6H_4$—O—$CH_2$—$C_6H_4$—$(O)_r$—R.

21. A method according to claim 1, wherein the X groups which do not represent a metal ion equivalent of atomic number 21–29, 42, 44 or 57–83 are individually lithium, potassium or sodium, or two such X groups are calcium or magnesium.

22. A method according to claim 1, wherein X groups which are not a metal ion equivalent of an element of atomic number 21–29, 42, 44 or 57–83 represent a salt with ethanolamine, diethanolamine, morpholine, glucamine, N,N-dimethylglucamine, N-methylglucamine, lysine, arginine, ornithine, lysine methylamide, glycine ethylamide or serine methylamide.

23. A method according to claim 11, wherein $Z^2$ is —$C_6H_4$—$OC_2H_5$ or —$C_2H_4$—$C_6H_5$—$OC_2H_5$.

24. A method according to claim 1, wherein said compound is administered in a dose of 1 μmole/kg–5 mmole/kg.

25. A method according to claim 24, wherein the dose of said compound is 10 μmole/kg–0.5 mmole/kg.

26. A method according to claim 1, wherein said compound is administered by intravenous injection.

27. A method according to claim 1, wherein said compound is administered orally.

28. A method according to claim 1, wherein at least one of k and r is 1.

29. A method according to claim 1, wherein said compound is administered as a pharmaceutical composition comprising said compound and a pharmaceutically acceptable carrier.

30. A method according to claim 1, wherein $R^1$ is H or $C_1$–$C_6$-alkyl.

31. A method of enhancing an NMR image of the GI tract of a patient comprising administering a compound of the formula

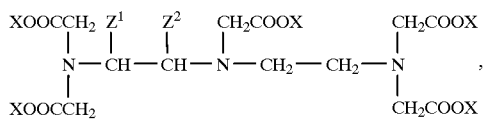

(I)

wherein
one of $Z^1$ and $Z^2$ is H and the other is

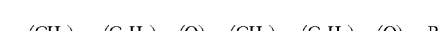

—$(CH_2)_m$—$(C_6H_4)_l$—$(O)_k$—$(CH_2)_n$—$(C_6H_4)_l$—$(O)_r$—R, wherein
m and n independently are 0–20,
k, l, q and r each independently is 0 or 1,
R is hydrogen, optionally $OR^1$-substituted $C_1$–$C_6$-alkyl or $CH_2COOR^1$,
$R^1$ is hydrogen, $C_1$–$C_6$-alkyl or benzyl, and X is, in each case, a hydrogen atom or a metal ion equivalent of an element of atomic number 21–29, 42, 44 or 58–70, with the provisos that:

at least two of the substituents X represent a metal ion equivalent of atomic number 21–29. 42, 44 or 58–70; and when n and l are each 0, then k and r are not each simultaneously 1;

—(O)$_r$—R is not —OH;

$Z^1$ and $Z^2$ are not —$C_6H_5$, —$CH_2$—$C_6H_5$, —$CH_2$—$C_6H_4$—O—$CH_2$—$COOCH_2C_6H_5$ or —$CH_2$—$C_6H_4$—O—$(CH_2)_5$—$COOCH_2C_6H_5$; and at least one of q and l is 1;

or a physiologically acceptable salt thereof with an inorganic and/or organic base, an amino acid or an amino acid amide.

32. A method according to claim 31, wherein said compound is administered as a pharmaceutical composition comprising said compound and a pharmaceutically acceptable carrier.

33. A method according to claim 31, wherein $R^1$ is H or $C_1$–$C_6$-alkyl.

34. A method of enhancing NMR imaging of a patient having renal insufficiency comprising administering to a patient a compound of the formula

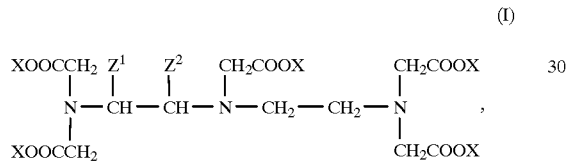

(I)

wherein one of $Z^1$ and $Z^2$ is H and the other is —$(CH_2)_m$—$(C_6H_4)_q$—$(O)_k$—$(CH_2)_n$—$(C_6H_4)_l$—$(O)_r$—R, wherein m and n, independently, are each 0–20, k, l, q and r are each, independently, 0 or 1, R is H, $C_1$–$C_6$-alkyl, $OR^1$-substituted $C_1$–$C_6$-alkyl or $CH_2COOR^1$, $R^1$ is H, $C_1$–$C_6$-alkyl or benzyl; and X is, in each case, a hydrogen atom or a metal ion equivalent of an element of atomic number 21–29, 42, 44 or 58–70;

with the provisos that:

at least two X groups represent a metal ion equivalent of atomic number 21–29, 42, 44 or 58–70;

when n and l are each 0, then k and r are not each simultaneously 1;

—(O)$_r$—R is not —OH;

$Z^1$ and $Z^2$ are not —$C_6H_5$, —$CH_2$—$C_6H_5$, —$CH_2$—$C_6H_4$—O—$CH_2$—$COOCH_2C_6H_5$ or —$CH_2$—$C_6H_4$—O—$(CH_2)_5$—$COOCH_2C_6H_5$; and at least one of q and l is 1;

or a physiologically acceptable salt thereof with an inorganic and/or organic base, an amino acid or an amino acid amide.

35. In a method of NMR imaging a patient comprising administering an NMR contrast agent to said patient, the improvement wherein said contrast agent is a compound of the formula

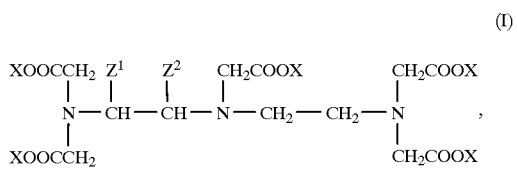

(I)

wherein one of $Z^1$ and $Z^2$ is H and the other is —$(CH_2)_m$—$(C_6H_4)_q$—$(O)_k$—$(CH_2)_n$—$(C_6H_4)_l$—$(O)_r$—R, wherein m and n, independently, are each 0–20, k, l, q and r are each, independently, 0 or 1, R is H, $C_1$–$C_6$-alkyl, $OR^1$-substituted $C_1$–$C_6$-alkyl or $CH_2COOR^1$, $R^1$ is H, $C_1$–$C_6$-alkyl or benzyl; and X is, in each case, a hydrogen atom or a metal ion equivalent of an element of atomic number 21–29, 42, 44 or 58–70;

with the provisos that:

at least two X groups represent a metal ion equivalent of atomic number 21–29, 42, 44 or 58–70;

when n and l are each 0, then k and r are not each simultaneously 1;

—(O)$_r$—R is not —OH;

$Z^1$ and $Z^2$ are not —$C_6H_5$, —$CH_2$—$C_6H_5$, —$CH_2$—$C_6H_4$—O—$CH_2$—$COOCH_2C_6H_5$ or —$CH_2$—$C_6H_4$—O—$(CH_2)_5$—$COOCH_2C_6H_5$; and at least one of q and l is 1;

or a physiologically acceptable salt thereof with an inorganic and/or organic base, an amino acid or an amino acid amide.

* * * * *

UNITED STATES PATENT AND TRADEMARK OFFICE
CERTIFICATE OF CORRECTION

PATENT NO. : 6,039,931
DATED : March 21, 2000
INVENTOR(S) : Schmitt-Williams et al.

It is certified that error appears in the above-identified patent and that said Letters Patent is hereby corrected as shown below:

Column 22, claim 20,
Line 2, reads "$(CH_2)$" should read -- $(CH_2)_m$ --

Signed and Sealed this

Ninth Day of April, 2002

Attest:

JAMES E. ROGAN
Attesting Officer  Director of the United States Patent and Trademark Office